United States Patent
Suka et al.

(10) Patent No.: US 10,975,042 B2
(45) Date of Patent: Apr. 13, 2021

(54) METHOD FOR PURIFYING AN AMINO ACID-N-CARBOXY ANHYDRIDE

(71) Applicant: SHIN-ETSU CHEMICAL CO., LTD., Tokyo (JP)

(72) Inventors: Yuki Suka, Joetsu (JP); Yuji Harada, Joetsu (JP); Shiori Nonaka, Joetsu (JP); Kazuomi Sato, Joetsu (JP); Takeru Watanabe, Joetsu (JP); Takehiko Ishii, Nagareyama (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/418,154

(22) Filed: May 21, 2019

(65) Prior Publication Data

US 2019/0359579 A1    Nov. 28, 2019

(30) Foreign Application Priority Data

May 25, 2018  (JP) .............................. JP2018-100816

(51) Int. Cl.
    *B01D 9/00*    (2006.01)
    *C07D 263/44*    (2006.01)

(52) U.S. Cl.
    CPC ............ *C07D 263/44* (2013.01); *B01D 9/004* (2013.01); *B01D 9/005* (2013.01); *B01D 9/0063* (2013.01)

(58) Field of Classification Search
    CPC ................................ B01D 9/00; C07D 263/44
    See application file for complete search history.

(56) References Cited

U.S. PATENT DOCUMENTS

| | | |
|---|---|---|
| 2002/0082431 A1 | 6/2002 | Cornille et al. |
| 2002/0183551 A1 | 12/2002 | Cornille et al. |
| 2004/0124144 A1 | 7/2004 | Paris et al. |
| 2006/0106229 A1 | 5/2006 | Carubia et al. |

FOREIGN PATENT DOCUMENTS

| | | |
|---|---|---|
| EP | 1 415 991 A1 | 5/2004 |
| JP | 2002-371070 A | 12/2002 |
| JP | 2004-149529 A | 5/2004 |
| JP | 4203786 B2 | 1/2009 |
| WO | 2006/047703 A2 | 5/2006 |

OTHER PUBLICATIONS

EP1415991—machine-translation, machine translation of EP 141599, 2004.*
Kricheldorf, Hans R. "Mechanismus der NCA-Polymerisation, 4*) Synthese und Reaktionen von N-Acyl-NCA**)." Makromol. Chemistry, vol. 178, pp. 905-939, 1977.
Lagrille, Olivier et al. "Process improvement in amino acid N-carboxyanhydride synthesis by N-carbamoyl amino acid nitrosation". Amino Acids, vol. 36, pp. 341-347, 2009.
Hirschmann, Ralph et al. "The Controlled Synthesis of Peptides in Aqueous Medium. The Preparation and Use of Novel α-Amino Acid N-Carboxyanhydride". Journal of the American Chemical Society, vol. 93, pp. 2746-2754, 1971.
Oct. 21, 2019 Extended European Search Report issued in European Patent Application No. 19176697.1.
Semple, Edward J. et al. "Large-scale synthesis of α-amino acid-N-carboxyanhydrides". Synthetic Communications, vol. 47, pp. 53-61, 2017.

* cited by examiner

*Primary Examiner* — Sun Jae Yoo
(74) *Attorney, Agent, or Firm* — Oliff PLC

(57) ABSTRACT

The present invention is a method for purifying an NCA, including the steps of: a) dissolving an NCA contaminated with impurities into a solvent which is a good solvent and is not a chlorinated solvent followed by stirring to precipitate an undissolved impurity to afford a suspension, b) adding an acidic filter aid having ability to trap a basic impurity to the obtained suspension followed by filtration and/or forming a fixed bed of the acidic filter aid having ability to trap a basic impurity followed by filtering the suspension to bring the suspension to be in contact with the acidic filter aid having ability to trap a basic impurity, and c) adding the obtained filtrate dropwise to a poor solvent for NCA to crystallize out the NCA in which the impurities are removed. This makes it possible to purify a low-purity NCA conveniently to afford a high-purity NCA.

13 Claims, 1 Drawing Sheet

[FIG. 1]
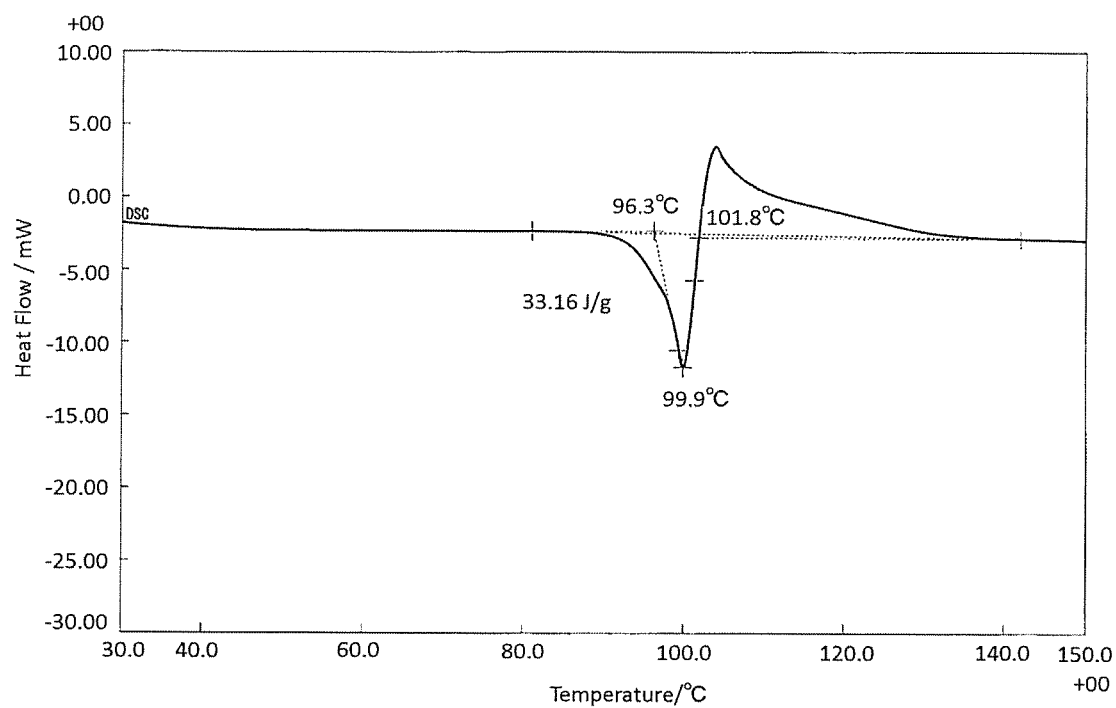
[FIG. 2]
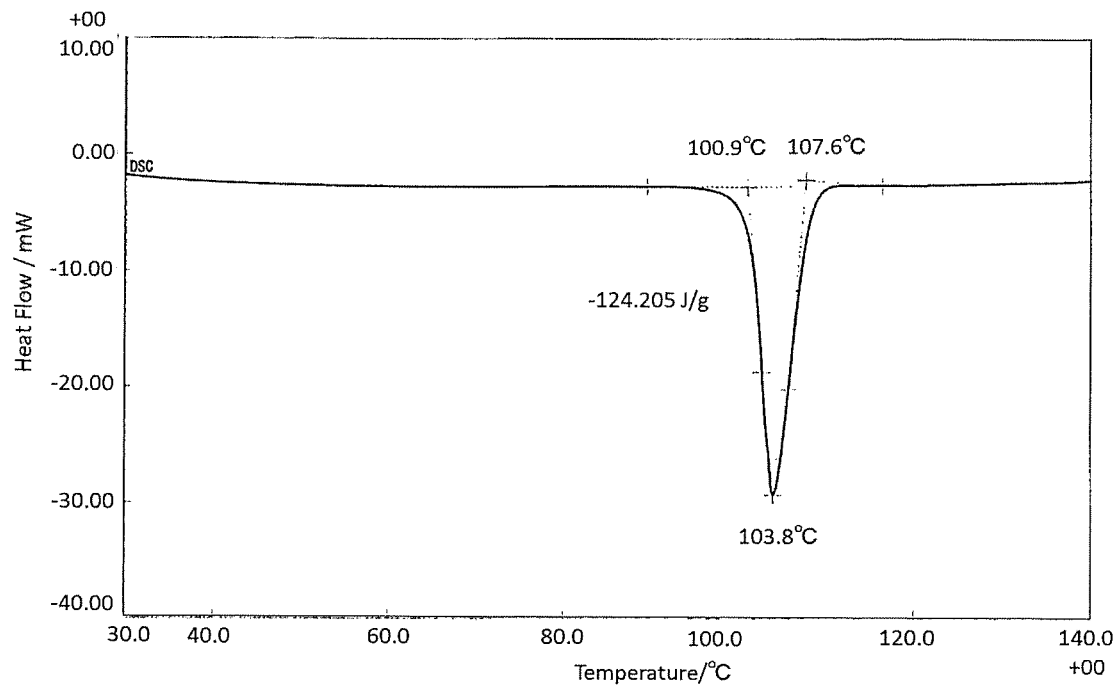

METHOD FOR PURIFYING AN AMINO ACID-N-CARBOXY ANHYDRIDE

TECHNICAL FIELD

The present invention relates to a method for purifying an amino acid-N-carboxy anhydride.

BACKGROUND ART

Amino acids, especially N-carboxy anhydrides (N-carboxyanhydride; hereinafter, abridged to NCA) obtained from α-, β-, or γ-amino acids are very useful intermediates because they each have an active acid anhydride group, and an amino group in each molecule is protected. This acid anhydride group can react with any nucleophilic units, so that it can react with an amino group to afford an amide group easily. Accordingly, they can be polymerized easily, thereby being useful for forming peptides. Alternatively, NCAs can easily form an ester bond through reaction with an alcohol and are also important to reduce the acid anhydride group.

The NCA has extremely high electrophilicity and gives polypeptide with a uniform molecular weight by living ring-opening polymerization initiated by amine. The initiator of amine is introduced into the terminal of polypeptide. Accordingly, various star-shaped polymers, graft copolymers, and block copolymers can be synthesized precisely by using a polyfunctional amine or a polymer having an amino group at the side chain or the terminal as an initiator. The obtained polypeptide is expected as a biocompatible material and can be block-copolymerized with hydrophilic polyethylene glycol to form a polymer micelle composed of a hydrophilic segment and a hydrophobic segment. This polymer micelle functions as a drug carrier by encapsulating the drug into the polymer micelle to give various effects including gradual release of the drug in a body and a concentrated dosage to a lesion, and is also useful in the field of drug delivery systems. The polypeptide also attracts enhanced interests in the peculiar self-organization due to its characteristic α-helix and a ρ-sheet structure, together with functions brought therefrom. In particular, having functions such as optical properties, piezoelectric properties, molecular permeability, and thermoresponsive properties, they are increasingly expected as next-generation materials such as electronics materials, liquid crystal materials, gas permeation materials, and high-performance fibers.

As for the synthesis of NCA, various methods have been reported. One of the most ordinary and direct method is a method of obtaining an NCA by reaction of amino acid or hydrochloric salt thereof and phosgene, diphosgene, or triphosgene in a solvent as expressed by the following reaction formula.

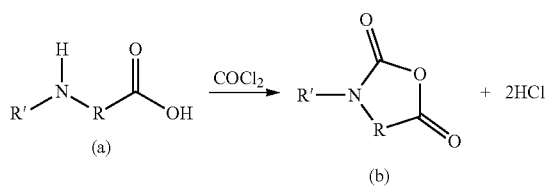

In the formula, R represents a central group between the acid group and the amino group of the amino acid, which may be modified; R' represents a hydrogen atom or a group bonded to the nitrogen atom in the amino acid; R and R' may be bonded with each other to form a cyclic amino acid structure.

In this reaction, it has been known that hydrogen chloride is formed, together with the NCA, in an amount of 2 mol per 1 mol of NCA. The hydrogen chloride, having higher reactivity, causes side reaction when it is contained in a medium to form a chlorinated by-product. These chlorinated by-products remain in the produced NCA to hinder polymerization reaction of the NCA seriously such as forming a bi-product and so on when the NCA is used for the polymerization reaction. The hydrogen chloride also acts as a stopper for a basic initiator. Accordingly, the amounts of chlorinated by-products and hydrogen chloride in an NCA monomer have to be sufficiently decreased in order to promote the polymerization precisely. The residual chlorine concentration is generally required to be 0.05 mass % or less.

The methods for decreasing the residual chlorine concentration in NCA include a method of decreasing the concentration in the stage of synthesizing an NCA and a method of purifying an NCA obtained by synthesis. Examples of the method of decreasing a residual chlorine concentration in the stage of synthesizing an NCA include a method of adding an unsaturated organic compound having an ethylenic double bond in the reaction of amino acid and phosgene to cause reaction of the produced hydrogen chloride and the unsaturated organic compound (Patent Document 1), together with a method of performing the reaction under reduced pressure to remove the produced hydrogen chloride (Patent Document 2). These methods make it possible to decrease the residual chlorine concentration to 0.05 mass % or less.

On the other hand, examples of the method of purifying an obtained NCA include a method in which an NCA is dissolved (or suspended) in a non-polar solvent, brought to be in contact with silica, and then taken out (Patent Document 3). This method makes it possible to afford a high-purity NCA in a higher yield, but the residual chlorine concentration is not described in the literature. This literature also describes treatment of the purified NCA with aqueous inorganic acid or organic acid solution to enhance the purity, but the treatment can causes a risk of forming by-products due to newly mixed acid and water. It employs a nonpolar solvent, and the soluble NCA is limited thereby. A recent report describes a method that allows NCA to be synthesized and purified in larger scale (Non-Patent Document 1). In this method, NCA is synthesized, and then purified by dissolving the NCA into dichloromethane, followed by filtration with weakly basic celite. This makes it possible to remove the residual chlorine to prevent forming of an NCA polymer due to the residual chlorine when the NCA is polymerized. However, the conceivable impurities contained in NCA include an impurity having a basic group such as an amino group, and the removal thereof has not been reported.

In currently commercially available NCAs, the residual chlorine concentration is rarely standardized to 0.05 mass % or less and is ascertained to vary depending on the production lot. They are also degraded largely with time and can form a polymer, especially after opening the package, caused by water in the air. Accordingly, the intended purity is frequently missed when using. In that case, additional purchase or re-purification is required, but cost increase cannot be avoided especially in the former case. Accordingly, it has been demanded to develop a convenient purification method to obtain NCA with stable residual chlorine concentration and purity.

CITATION LIST

Patent Literature

Patent Document 1: Japanese Patent No. 4203786
Patent Document 2: Japanese Unexamined Patent Application Publication No. 2002-371070
Patent Document 3: Japanese Unexamined Patent Application Publication No. 2004-149529

Non-Patent Literature

Non Patent Document 1: Syn. Commun. 2017, VOL. 47, NO. 1, 53-61

SUMMARY OF INVENTION

Technical Problem

The present invention was accomplished to solve the above-described subjects. It is an object of the present invention to provide a method for purifying an amino acid-N-carboxyanhydride (NCA) by which a low-purity NCA can be purified conveniently to afford a high-purity NCA.

Solution to Problem

To solve the foregoing subjects, the present invention provides a method for purifying an amino acid-N-carboxyanhydride shown by the following general formula (1):

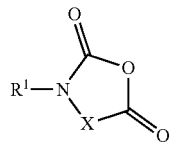

(I)

wherein $R^2$ represents a hydrogen atom, an alkyl group optionally having a substituent, a cycloalkyl group optionally having a substituent, an aryl group optionally having a substituent, a hetero ring optionally having a substituent, or a commonly used protective group for an amino acid selected from a benzyloxycarbonyl group, a t-butoxycarbonyl group, a benzoyl group, and an acetyl group, provided that $R^2$ does not contain a reactive group of unprotected hydroxy group nor a reactive group of unprotected amino group; X is shown by the following general formula (i) and represents a divalent hydrocarbon group optionally having a substituent, provided that X does not contain a reactive group of unprotected hydroxy group nor a reactive group of unprotected amino group; and $R^2$ and X are optionally bonded with each other to form a cyclic amino acid structure,

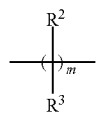

(I)

wherein $R^2$ and $R^3$ each independently represent a hydrogen atom, an alkyl group optionally having a substituent, a cycloalkyl group optionally having a substituent, an aryl group optionally having a substituent, or a hetero ring optionally having a substituent; and "m" is an integer of 1 to 3, the method comprising the steps of:
a) dissolving the amino acid-N-carboxyanhydride contaminated with impurities into a solvent which is a good solvent for the amino acid-N-carboxyanhydride and is not a chlorinated solvent followed by stirring to precipitate an undissolved impurity to afford a suspension,
b) adding an acidic filter aid having ability to trap a basic impurity to the suspension obtained in the step a) followed by filtration and/or forming a fixed bed of the acidic filter aid having ability to trap a basic impurity followed by filtering the suspension to bring the suspension to be in contact with the acidic filter aid having ability to trap a basic impurity, and
c) adding the filtrate obtained by the step b) dropwise to a poor solvent for the amino acid-N-carboxyanhydride to crystallize out the amino acid-N-carboxyanhydride in which the impurities are removed.

Using amino acid-N-carboxyanhydride that has no (or a protected) reactive group, the purification method described above makes it possible to purify a low-purity NCA conveniently to give a high-purity NCA.

It is preferable that the acidic filter aid having ability to trap a basic impurity used in the step b) be selected from magnesium sulfate, calcium sulfate, barium sulfate, copper sulfate, and silica gel having a surface modified with sulfonic acid or carboxylic acid.

Using these acidic filter aid having ability to trap a basic impurity(s), it becomes possible to afford an amino acid-N-carboxyanhydride with higher purity in which impurities are further removed.

It is preferable that the amino acid-N-carboxyanhydride be α-amino acid-N-carboxyanhydride, with the "m" being 1.

The amino acid-N-carboxyanhydride like this can be conveniently purified by the present invention. Such an amino acid-N-carboxyanhydride is preferable for affording a polypeptide derivatives that can be generally used.

It is preferable that the amino acid-N-carboxyanhydride is a compound shown by any of the following structural formulae:

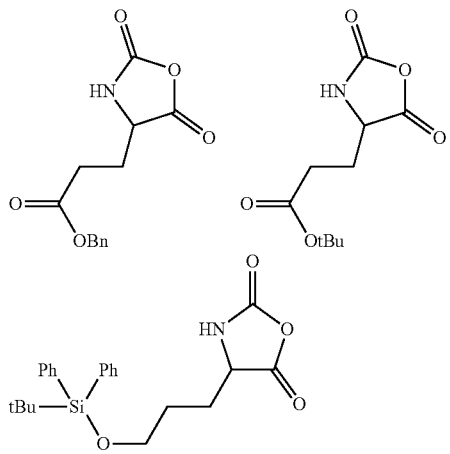

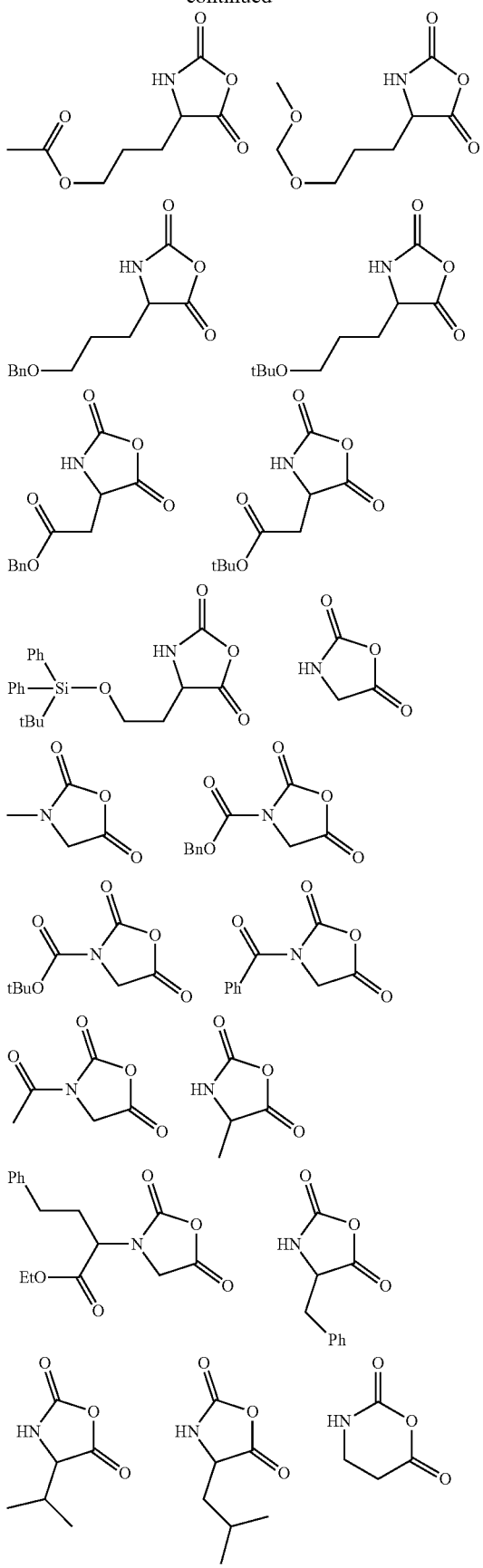

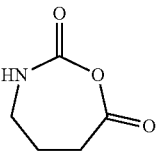

wherein Bn represents a benzyl group, tBu represents a tert-butyl group, Et represents an ethyl group, and Ph represents a phenyl group.

These amino acid-N-carboxyanhydrides can be conveniently purified by the present invention.

It is preferable that a mass of the good solvent for the amino acid-N-carboxyanhydride used in the step a) be 1 time or more relative to a mass of the used amino acid-N-carboxyanhydride.

It is preferable that the good solvent for the amino acid-N-carboxyanhydride used in the step a) be a polar solvent selected from tetrahydrofuran, 1,4-dioxane, ethyl acetate, n-butyl acetate, γ-butyrolactone, acetone, methyl ethyl ketone, methyl isobutyl ketone, dimethyl sulfoxide, N,N-dimethylformamide, and acetonitrile.

These good solvents can dissolve the amino acid-N-carboxyanhydride more readily and have higher effect to precipitate undissolved impurities, thereby making it possible to afford an amino acid-N-carboxyanhydride with higher purity in which impurities are removed.

It is preferable that a mass of the poor solvent for the amino acid-N-carboxyanhydride used in the step c) be 2 times or more relative to a mass of the used amino acid-N-carboxyanhydride.

It is preferable that the poor solvent for the amino acid-N-carboxyanhydride used in the step c) be a solvent selected from n-hexane, n-heptane, n-octane, n-nonane, n-decane, cyclopentane, cyclohexane, cycloheptane, cyclooctane, diethyl ether, diisopropyl ether, and t-butyl methyl ether.

These poor solvents make it possible to crystallize out the amino acid-N-carboxyanhydride more efficiently.

It is preferable that the amino acid-N-carboxyanhydride in which the impurities are removed have a residual chlorine concentration of 0.05 mass % or less.

It is preferable that the amino acid-N-carboxyanhydride in which the impurities are removed have a residual chlorine concentration of 0.01 mass % or less.

As described above, the present invention makes it possible to afford an amino acid-N-carboxyanhydride with decreased residual chlorine concentration.

It is preferable that the amino acid-N-carboxyanhydride in which the impurities are removed have a purity of 98 mol % or more measured by differential scanning calorimetry.

Having such purity, when the amino acid-N-carboxyanhydride in which impurities are removed is used for polymerization reaction, formation of by-product of low molecular weight NCA homopolymer can be more suppressed.

It is preferable that the steps a), b), and c) be performed in the air.

Having these steps a), b), and c), the purification operation does not have to be performed in a nitrogen atmosphere and can be operated in the air to improve the convenience largely.

Advantageous Effects of Invention

As described above, the inventive method for purifying an amino acid-N-carboxyanhydride (NCA) makes it possible to purify a low-purity NCA conveniently to afford a high-purity NCA. In the method for purifying an NCA of the present invention, the purification does not have to be performed in a nitrogen atmosphere and can also be operated in the air to improve the convenience largely.

BRIEF DESCRIPTION OF DRAWINGS

FIG. 1 is an example of results of DSC measurement of an amino acid-N-carboxyanhydride contaminated with impurities;

FIG. 2 is an example of results of DSC measurement of an amino acid-N-carboxyanhydride in which impurities are removed.

DESCRIPTION OF EMBODIMENTS

As described above, it has been demanded a method for purifying an amino acid-N-carboxyanhydride (NCA) by which a low-purity NCA can be purified conveniently to afford a high-purity NCA.

The present inventors have diligently investigated to achieve the above objects to find that an undissolved impurity(s) and a basic impurity(s) can be removed to afford a high-purity NCA by dissolving the NCA to a solvent initially followed by stirring to precipitate an insoluble polymer(s) and impurities of hydrochloric acid salt (undissolved impurities) to give a suspension, and then bringing the suspension to be in contact with an acidic filter aid having ability to trap basic impurities, particularly magnesium sulfate to filter the suspension. It has been known that the NCA is hydrolyzed by water in the air to lower the purity. Since the filter aid having ability to trap basic impurities also effects dehydration, the purification does not have to be operated in a nitrogen atmosphere, and successfully affords a high-purity NCA even when the purification is performed in the air.

That is, the present invention is a method for purifying an amino acid-N-carboxyanhydride shown by the following general formula (1):

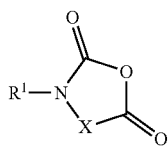
(I)

wherein $R^1$ represents a hydrogen atom, an alkyl group optionally having a substituent, a cycloalkyl group optionally having a substituent, an aryl group optionally having a substituent, a hetero ring residue optionally having a substituent, or a protective group for an amino acid selected from a benzyloxycarbonyl group, a t-butoxycarbonyl group, a benzoyl group, and an acetyl group, provided that $R^1$ does not contain a reactive group of unprotected hydroxy group nor a reactive group of unprotected amino group; X is shown by the following general formula (a) and represents a divalent hydrocarbon group optionally having a substituent, provided that X does not contain a reactive group of unprotected hydroxy group nor a reactive group of unprotected amino group; and $R^2$ and X are optionally bonded with each other to form a cyclic amino acid structure,

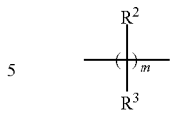
(a)

wherein $R^2$ and $R^3$ each independently represent a hydrogen atom, an alkyl group optionally having a substituent, a cycloalkyl group optionally having a substituent, an aryl group optionally having a substituent, or a hetero ring residue optionally having a substituent; and "m" is an integer of 1 to 3, the method comprising the steps of:

a) dissolving the amino acid-N-carboxyanhydride contaminated with impurities into a solvent which is a good solvent for the amino acid-N-carboxyanhydride and is not a chlorinated solvent followed by stirring to precipitate an undissolved impurity to afford a suspension, b) adding an acidic filter aid having ability to trap basic impurities to the suspension obtained in the step a) followed by filtration and/or forming a fixed bed of the acidic filter aid having ability to trap basic impurities followed by filtering the suspension to bring the suspension to be in contact with the acidic filter aid having ability to trap basic impurities, and c) adding the filtrate obtained by the step b) dropwise to a poor solvent for the amino acid-N-carboxyanhydride to crystallize the amino acid-N-carboxyanhydride in which the impurities are removed.

Hereinafter, the inventive method for purifying an amino acid-N-carboxyanhydride (NCA) will be described specifically, but the present invention is not limited thereto.

<<Method for Purifying an Amino Acid-N-Carboxyanhydride>>

The inventive method for purifying an amino acid-N-carboxyanhydride includes the steps a), b), and c) described above. Hereinafter, the amino acid-N-carboxyanhydride and each step will be described more specifically.

[Amino Acid-N-Carboxyanhydride]

The NCA purified by the present invention is any NCA derived from natural or synthetic amino acids. This NCA can be expressed by the general formula (I), and the reactive group have to be protected. When the reactive group is not protected, the reactive group can react with an NCA. As this NCA, any type can be used including various kinds of stereochemical structures, particularly when the NCA has a single or a plurality of asymmetric carbon atom, such as racemic compounds, mirror image isomers, and diastereomers. The inventive purification method does not cause racemization, and an isomer can be obtained having the same configuration as in the start material.

Illustrative examples of the compound shown by the general formula (I) include the following compounds, which is synthesized from α-amino acid (m=1), β-amino acid (m=2), or γ-amino acid (m=3), but not limited thereto. Among them, the NCA synthesized from α-amino acid is preferable.

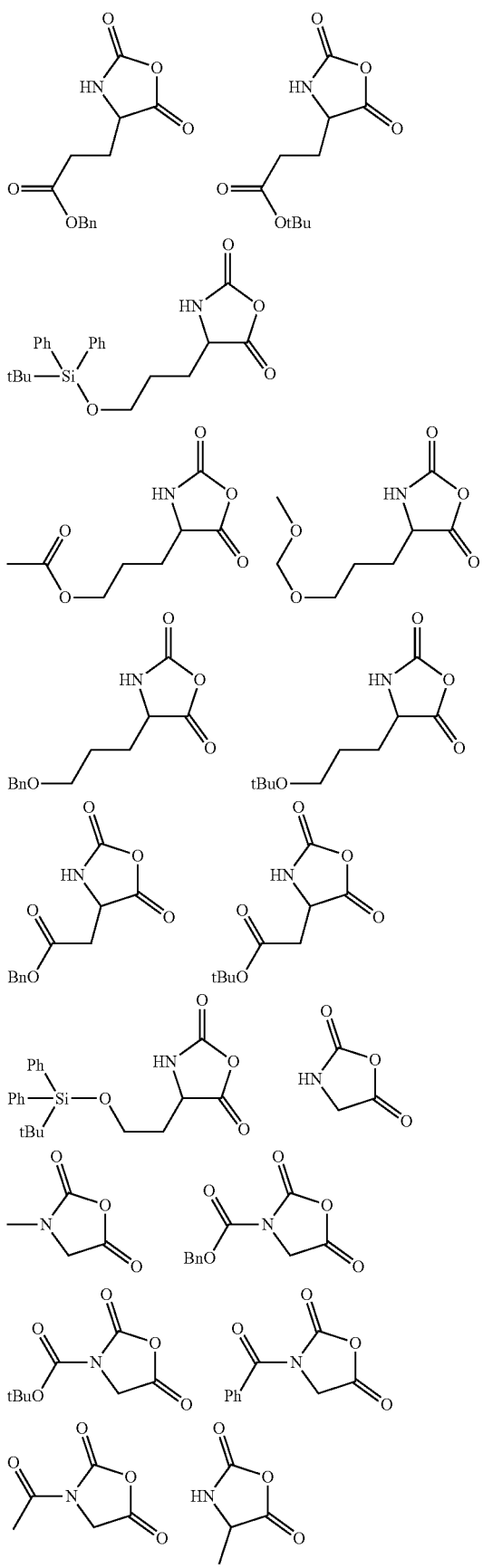
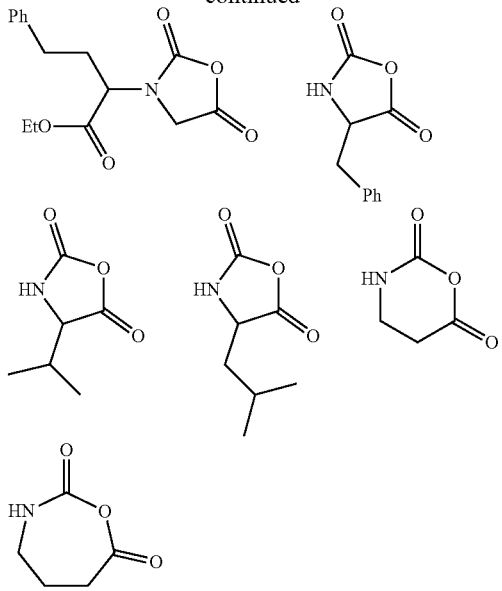

In the formulae, Bn represents a benzyl group, tBu represents a tert-butyl group, Et represents an ethyl group, and Ph represents a phenyl group.

[Step a)]

The step a) is a step of dissolving the amino acid-N-carboxyanhydride contaminated with impurities into a solvent which is a good solvent for the amino acid-N-carboxyanhydride and is not a chlorinated solvent, followed by stirring to precipitate an undissolved impurity to afford a suspension.

<Good Solvent>

The solvent used in the step a) is not particularly limited if the solvent is a good solvent for NCA, that is, a solvent that can dissolve NCA, without dissolving impurities of a polymer or hydrochloric acid salt (undissolved impurities). Illustrative examples thereof include a polar solvents, for example, ethers such as tetrahydrofuran, 1,4-dioxane, etc.; esters such as ethyl acetate, n-butyl acetate, γ-butyrolactone, etc.; ketones such as acetone, methyl ethyl ketone, methyl isobutyl ketone, etc.; dimethyl sulfoxide (DMSO), N,N-dimethylformamide (DMF), acetonitrile, etc. Among them, tetrahydrofuran and ethyl acetate are preferable. However, chlorinated solvent such as chloroform and dichloromethane are not preferable because they can increase the residual chlorine concentration.

The amount of the good solvent to be used is not particularly limited, and is, for example, 1 to 20 times, preferably 2 to 10 times, more preferably 2 to 5 times relative to the mass of the NCA.

The method to determine that the solvent is a good solvent for NCA includes a method of adding a good solvent to NCA with stirring, followed by visual observation to confirm that the NCA has been dissolved without forming turbidity, but is not particularly limited if complete dissolution can be determined by the method. In this case, the amount of the good solvent is not particularly limited, and is, for example, 0.1 to 200 times, preferably 1 to 20 times, more preferably 1 to 10 times relative to the mass of NCA.

<Undissolved Impurities>

In the step a), the undissolved impurities that is insoluble to the above solvent include a polymer of NCA, which is formed by reaction initiated by a chloride ion, hydrochloric acid salt of a raw material amino acid, etc., but are not particularly limited, including any component that is insoluble to the above solvent.

[Step b)]

The step b) is a step of adding an acidic filter aid having ability to trap a basic impurity to the suspension obtained in the step a) followed by filtration and/or forming a fixed bed of the acidic filter aid having ability to trap a basic impurity followed by filtering the suspension to bring the suspension to be in contact with the acidic filter aid having ability to trap a basic impurity.

<Acidic Filter Aid Having Ability to Trap Basic Impurity>

The filtration of undissolved impurity precipitated in the step a) causes clogging on a filter plate without using a filter aid to make the filterability markedly worse, and accordingly, a filter aid is required. In order to remove a basic impurity(s) described below, the filter aid is to be an acidic filter aid having ability to trap a basic impurity. Though the acidic filter aid having ability to trap a basic impurity possesses an effect for purifying an NCA (effect for removing a basic impurity) only by addition to the suspension, it is preferable to form a fixed bed on a filter plate in order to obtain an NCA with higher purity.

The acidic filter aid having ability to trap a basic impurity used in the step b) is not particularly limited if it can remove a basic impurity (impurity having a basic group such as an amino group). Illustrative examples thereof include magnesium sulfate, calcium sulfate, barium sulfate, copper sulfate, and silica gel having a surface modified with sulfonic acid or carboxylic acid. Illustrative examples of the silica gel having a surface modified with sulfonic acid or carboxylic acid include ACD silica and DPR silica manufactured by FUJI SILYSIA CHEMICAL LTD. However, chlorides such as magnesium chloride and calcium chloride are not preferable in view of a residual chlorine concentration. It is to be noted that the acidic filter aid having ability to trap a basic impurity possesses an effect to trap a basic impurity(s) to prevent polymerization of forming an NCA homopolymer, but the effect is not achieved with the silica exemplified in Patent Document 3 (the traditional one used for chromatography) as shown in polymerization inhibiting test that will be described below. In case of using DPR silica after forming a fixed bed on a filter plate, an NCA is adsorbed by the silica gel. Accordingly, the filtration requires washing with excess amount of solvent. Since this makes concentration inevitable, magnesium sulfate is more preferable as a fixed bed in view of convenience.

Additionally, the acidic filter aid having ability to trap a basic impurity also possesses a dehydration effect not only removing the basic impurity(s), thereby making it possible to remove water brought from the air in operating purification to prevent an NCA from hydrolysis. Accordingly, the operation can be performed with a convenient apparatus not only in a nitrogen atmosphere.

The amount of the acidic filter aid to be used is not particularly limited, and is, for example 0.1 to 20 times, preferably 1 to 10 times, more preferably 1 to 5 times relative to the mass of the NCA. The acidic filter aid having ability to trap a basic impurity may be used alone or in combination with two or more kinds.

<Basic Impurity>

Illustrative examples of the basic impurity having a basic group such as an amino group include the basic compound (c) formed by the following reaction formula, but are not particularly limited if it has basicity.

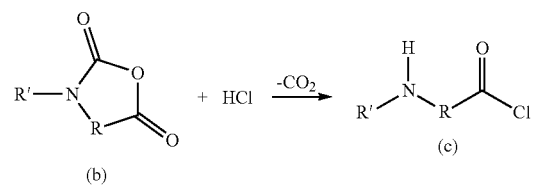

(b) + HCl $\xrightarrow{-CO_2}$ (c)

In the formula, R represents a central group between the acid group and the amino group of the amino acid, which may be modified; R' represents a hydrogen atom or a group bonded to the nitrogen atom in the amino acid; R and R' may be bonded with each other to form a cyclic amino acid structure.

[Step c)]

The step c) is a step of adding the filtrate obtained by the step b) dropwise to a poor solvent for the amino acid-N-carboxyanhydride, thereby crystallizing out to afford an amino acid-N-carboxyanhydride in which the impurities are removed.

<Poor Solvent>

The poor solvent used in the step c) is not particularly limited if an NCA has lower solubility thereto. Illustrative examples thereof include hydrocarbons such as n-hexane, n-heptane, n-octane, n-nonane, n-decane, cyclopentane, cyclohexane, cycloheptane, cyclooctane, etc.; and ethers such as diethyl ether, diisopropyl ether, t-butyl methyl ether, etc. Among them, n-hexane and n-heptane are preferable.

The amount of the solvent to be used is not particularly limited, and is, for example, 2 to 80 times, preferably 4 to 40 times, more preferably 4 to 20 times relative to the mass of the NCA.

<Crystallization>

The crystallization in the step c) can be performed by dropwise addition of the filtrate intact to a poor solvent or by dropwise addition to a poor solvent subsequent to concentration to adjust the concentration. The temperature for conducting the crystallization is not particularly limited, but is preferably room temperature in view of the convenience of operation. Herein, "crystallization" is an operation different from ordinary "recrystallization", in which an NCA is dissolved in a good solvent, and then a poor solvent is added thereto, followed by decreasing the temperature of the solution to separate out the crystal. In comparison to the recrystallization, which requires a precise and time consuming operation to crystallize out, the crystallization is convenient, and is performable in industrial scale thereby.

The NCA obtained by crystallization is filtered, and then may be subjected to vacuum drying as it is or subjected to vacuum drying after it is washed with a poor solvent. The poor solvent used for the washing is not particularly limited if an NCA shows lower solubility thereto, and can be the same poor solvent as the one used for the crystallization. The temperature for washing is not particularly limited, but is preferably room temperature in view of the convenience of operation. The temperature for drying is not particularly limited, and is, for example 0 to 40° C., preferably room temperature.

The method to determine that the solvent is a poor solvent for NCA is not particularly limited if total insolubility can be confirmed, including a method of adding a poor solvent to NCA with stirring, followed by confirming that the NCA is not dissolved at all and turbidity is not observed by visual inspection. In this case, the amount of the poor solvent is not particularly limited, and is, for example, 0.2 to 800 times, preferably 2 to 80 times, more preferably 2 to 20 times relative to the mass of NCA.

As described above, by the inventive method for purifying an amino acid-N-carboxyanhydride, an undissolved impurity(s) that is insoluble to a solvent (an NCA polymer, hydrochloric acid salt, etc. due to residual chlorine) is successfully removed by filtration, and a basic impurity(s) having an amino group due to ring-opening by hydrolysis and so on can be removed with the acidic filter aid having ability to trap a basic impurity. The acidic filter aid having ability to trap a basic impurity like this also has hygroscopicity, thereby making it possible to prevent an influence of water in the air to perform the purification in the air to largely improve the convenience. Additionally, the crystallization of NCA is successfully performed only by dropwise addition of filtrate to a poor solvent followed by stirring and does not need time consuming and precise recrystallization, and accordingly, production can be performed in industrial scale.

EXAMPLE

Reference Example

Each ability to trap a basic impurity was determined regarding acidic filter aids having ability to trap a basic impurity, other filter aids, and other additives on the basis of each ability to inhibit polymerization. As the NCA, the compound shown by the following structural formula (A) was used. First, 0.2 g (0.87 mmol) of NCA was dissolved in 1.0 g of ethyl acetate to prepare an NCA solution. Using this NCA solution, Comparison 1 was prepared without adding additives as shown in Table 1, and Comparisons 2 to 5 were prepared by adding general silica gel (Silica gel 60 for column chromatography manufactured by KANTO CHEMICAL CO., INC.), organic acid (acetic acid), inorganic acid (hydrogen chloride solution in ethyl acetate), and Celite 503 (weakly basic) respectively. In a similar manner, Experiment 1 and Experiment 2 were prepared by adding magnesium sulfate (anhydrous) and DPR (De-Protector) silica (manufactured by FUJI SILYSIA CHEMICAL LTD.) respectively as an acidic filter aid having ability to trap a basic impurity. They are left for a prescribed time at each temperature, and the viscosity change of each NCA solution was visually observed. The results are shown in Table 1.

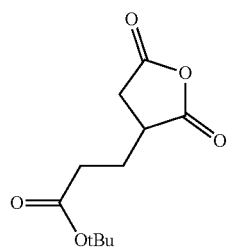

(A)

Residual chlorine concentration: 0.091 mass %
Melting point: 99.9° C.

TABLE 1

| Experiment No. | Filter aid/Additive | Amount | Ordinal temp. (1 h) | 40° C. (5 min.) | 60° C. (5 min.) |
|---|---|---|---|---|---|
| Comparative 1 | — | — | No change | No change | Viscosity increased |
| Comparative 2 | Silica gel 60 | 67 mg | No change | No change | Viscosity increased |
| Comparative 3 | Acetic acid | 6 mg (0.1 mmol) | No change | Viscosity increased | Viscosity further increased |
| Comparative 4 | HCl in AcOEt (1 mol/L) | 100 µl (0.1 mmol) | No change | No change | No change |
| Comparative 5 | Celite 503 | 67 mg | No change | No change | Viscosity increased |
| Experiment 1 | Magnesium sulfate | 67 mg | No change | No change | No change |
| Experiment 2 | DPR silica | 67 mg | No change | No change | No change |

In Comparative 1 without adding an additive, a viscosity increase was observed to confirm that polymerization reaction had occurred. In each of Comparative 2 and Comparative 5, using general silica gel and Celite 503, a viscosity increase was observed to reveal that they did not effect to inhibit polymerization. On the other hand, in case of adding magnesium sulfate or DPR silica, which are acidic filter aids having ability to trap a basic impurity, as in Examples 1 and 2, each viscosity did not change to reveal that they effected to inhibit polymerization. In Comparative 4, addition of HCl also showed an effect for inhibiting polymerization, but the residual HCl after the purification causes to form basic impurities and is not preferable thereby. In case of adding acetic acid (Comparative 3), which is an organic acid, the viscosity increase was large to reveal that the polymerization was further accelerated.

Hereinafter, the present invention will be specifically described by showing Examples and Comparative Examples, but the present invention is not limited to the following examples.

[Measurement of Residual Chlorine Concentration]

In Examples and Comparative Examples, each residual chlorine concentration was measured in accordance with the following official methods: ASTM D5808, JPI 5S-64-02, and TS K0010 using a trace chlorine analyzer TCL-2100V (manufactured by Mitsubishi Chemical Analytec Co., Ltd.).

[Measurement of Purity]

In Examples and Comparative Examples, the purity of each NCA was measured using differential scanning calorimeter (DSC) in accordance with 2.52 thermal analysis method of The Japanese Pharmacopoeia, 17$^{th}$ ed. (2.4.4. measurement of purity). The measurement was performed using Thermo plus EVO DSC8230 (manufactured by Rigalu Corporation) as a measurement apparatus with the sample amount of 1 mg at a temperature increasing rate of 1° C./minute. Incidentally, it is conceived that precise measurement cannot be guaranteed unless the purity is 98 mol % or more according to 2.52 thermal analysis method of The Japanese Pharmacopoeia, 17$^{th}$ ed. (2.4.4. measurement of purity).

Example 1

To 5.02 g of NCA shown by the structural formula (A), 1.70 g of magnesium sulfate and 24.96 g of ethyl acetate were added. This was stirred to dissolve the NCA and to precipitate undissolved impurities to prepare a suspension.

Then, this suspension was poured into a filter stacked with 15.00 g of magnesium sulfate, and vacuum filtration was performed (including sufficient washing with ethyl acetate) to remove the precipitate to afford 33.05 g of colorless transparent filtrate. This filtrate was added dropwise to 112 g of n-hexane to perform crystallization. The white powder thus formed was filtered, and then washed with 50 g of n-hexane twice. Incidentally, these operations were performed in the air not in a nitrogen atmosphere, and the work took time about 30 minutes. The obtained white powder was vacuum dried at ordinary temperature to afford 3.50 g of NCA in which impurities were removed. The purity of NCA in which impurities were removed was 98.93 mol % determined by DSC measurement (melting point: 103.8° C.), and the residual chlorine concentration was 0.005 mass %. The NCA before purification, that is, the NCA contaminated with impurities was too low in purity, and the purity could not be determined by DSC measurement (melting point: 99.9° C.) thereby, but the measured results are shown in FIG. 1. The results similarly measured for the NCA in which impurities were removed are shown in FIG. 2.

In order to determine the solubility of NCA to ethyl acetate, which is a good solvent, 0.2 g of the purified NCA shown by the structural formula (A) was dissolved in 1.0 g of ethyl acetate. As a result, undissolved impurity was not determined visually. In the NCA equally shown by the structural formula (A) but before purification, undissolved impurities were determined visually. On the other hand, in order to determine the solubility of NCA to n-hexane, which is a poor solvent, 0.2 g of the purified NCA shown by the structural formula (A) was tried to be dissolved in 2.0 g of n-hexane. As a result, dissolution was not determined visually.

Example 2

In the same way as in Example 1 except for changing the good solvent used for dissolving NCA from ethyl acetate to tetrahydrofuran, 3.42 g of NCA in which impurities were removed was obtained. The purity of NCA in which impurities were removed was 98.90 mol % determined by DSC measurement (melting point: 103.8° C.), and the residual chlorine concentration was 0.006 mass %.

Example 3

To 5.00 g of NCA shown by the structural formula (A), 1.70 g of DPR silica and 25.00 g of ethyl acetate were added. This was stirred to dissolve the NCA and to precipitate undissolved impurities to prepare a suspension. Then, this suspension was poured into a filter stacked with 15.00 g of magnesium sulfate, and vacuum filtration was performed (including sufficient washing with ethyl acetate) to remove the precipitate to afford 33.50 g of colorless transparent filtrate. This filtrate was added dropwise to 114 g of n-hexane to perform crystallization. The white powder thus formed was filtered, and then washed with 50 g of n-hexane twice. Incidentally, these operations were performed in the air not in a nitrogen atmosphere, and the work took time about 30 minutes. The obtained white powder was vacuum dried at ordinary temperature to afford 3.40 g of NCA in which impurities were removed. The purity of NCA in which impurities were removed was 99.05 mol % determined by DSC measurement (melting point: 104.3° C.), and the residual chlorine concentration was 0.003 mass %.

Example 4

To 5.00 g of NCA shown by the structural formula (A), 1.70 g of DPR silica and 25.00 g of ethyl acetate were added. This was stirred to dissolve the NCA and to precipitate undissolved impurities to prepare a suspension. Then, this suspension was poured into a filter stacked with 15.00 g of DPR silica, and vacuum filtration was performed (including sufficient washing with ethyl acetate) to remove the precipitate to afford 80.00 g of colorless transparent filtrate. This filtrate was concentrated to 30.00 g at 30° C. under reduced pressure, and then added dropwise to 100 g of n-hexane to perform crystallization. The white powder thus formed was filtered, and then washed with 50 g of n-hexane twice. The obtained white powder was vacuum dried at ordinary temperature to afford 3.00 g of NCA in which impurities were removed. The purity of NCA in which impurities were removed was 99.15 mol % determined by DSC measurement (melting point: 104.2° C.), and the residual chlorine concentration was 0.002 mass %.

Example 5

To 5.01 g of NCA shown by the structural formula (A), 1.70 g of magnesium sulfate and 24.99 g of ethyl acetate were added. This was stirred to dissolve the NCA and to precipitate undissolved impurities to prepare a suspension. Then, this suspension was poured onto a filter paper, and vacuum filtration was performed (including sufficient washing with ethyl acetate) to remove the precipitate to afford 30.05 g of colorless transparent filtrate. This filtrate was added dropwise to 100 g of n-hexane to perform crystallization. The white powder thus formed was filtered, and then washed with 50 g of n-hexane twice. Incidentally, these operations were performed in the air not in a nitrogen atmosphere, and the work took time about 30 minutes. The obtained white powder was vacuum dried at ordinary temperature to afford 3.80 g of NCA in which impurities were removed. The purity of NCA in which impurities were removed was 98.25 mol % determined by DSC measurement (melting point: 103.2° C.), and the residual chlorine concentration was 0.030 mass %.

Example 6

To 200 g of NCA shown by the structural formula (A), 67 g of magnesium sulfate and 600 g of ethyl acetate were added. This was stirred to dissolve the NCA and to precipitate undissolved impurities to prepare a suspension. Then, this suspension was poured into a filter stacked with 600 g of magnesium sulfate, and vacuum filtration was performed (including sufficient washing with ethyl acetate) to remove the precipitate to afford 1000 g of colorless transparent filtrate. This filtrate was added dropwise to 3200 g of n-hexane to perform crystallization. The white powder thus formed was filtered, and then washed with 1000 g of n-hexane twice. Incidentally, these operations were performed in the air not in a nitrogen atmosphere, and the work took time about 2 hours. The obtained white powder was vacuum dried at ordinary temperature to afford 160 g of NCA in which impurities were removed. The purity of NCA in which impurities were removed was 99.46 mol % determined by DSC measurement (melting point: 104.3° C.), and the residual chlorine concentration was 0.001 mass % or less.

Examples 7 to 23

In the same way as in Example 2 except that the NCA of (A) contaminated with impurities was changed to (B) to (R), NCAs in which impurities were removed were obtained. As a method to determine the solubility to a good solvent, 0.2 g of each NCA before or after the purification was added to 1.0 g of tetrahydrofuran. On the other hand, as a method to determine the solubility to a poor solvent, 2.0 g of n-hexane was added to 0.2 g of each NCA after purification. The results are shown in Table 2, wherein "good" represents that no undissolved matter was observed, and "inferior" represents that turbidity or undissolved matter was observed.

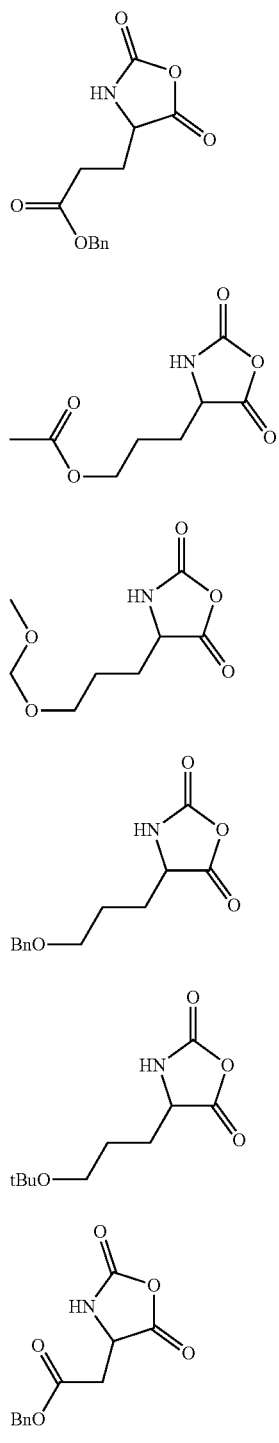
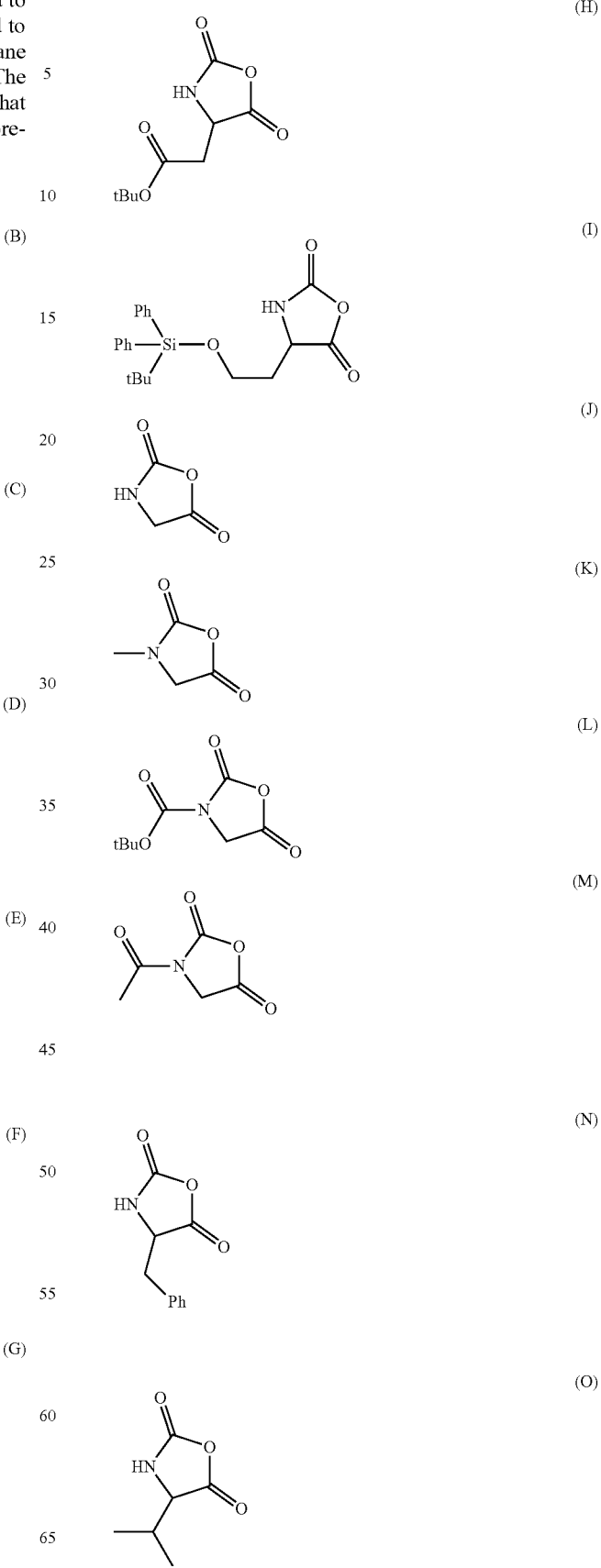

-continued

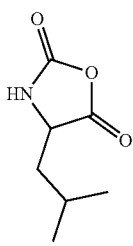
(P)

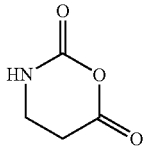
(Q)

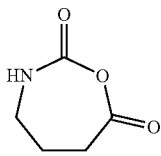
(R)

In the formulae, Bn represents a benzyl group, tBu represents a tert-butyl group, and Ph represents a phenyl group.

residual chlorine concentration in commercially available NCAs. It is to be noted that the commercially available NCA with the residual chlorine concentration being more than 0.050 mass %, which is not described because the initial purity was 98 mol % or less, showed lowering of the melting point with the passage of time to reveal that the purity was lowered.

TABLE 2

| NCA | Residual chlorine concentration before purification (mass %) | Residual chlorine concentration after purification (mass %) | Purity after purification (mol %) | Solubility to good solvent before purification | Solubility to good solvent after purification | Solubility to poor solvent after purification |
|---|---|---|---|---|---|---|
| (B) | 0.070 | ≤0.001 | 99.40 | inferior | good | inferior |
| (C) | 0.085 | 0.001 | 99.20 | inferior | good | inferior |
| (D) | 0.100 | 0.004 | 99.00 | inferior | good | inferior |
| (E) | 0.115 | 0.005 | 98.90 | inferior | good | inferior |
| (F) | 0.090 | 0.002 | 99.10 | inferior | good | inferior |
| (G) | 0.075 | ≤0.001 | 99.25 | inferior | good | inferior |
| (H) | 0.088 | 0.001 | 99.18 | inferior | good | inferior |
| (I) | 0.080 | ≤0.001 | 99.35 | inferior | good | inferior |
| (J) | 0.090 | 0.002 | 99.10 | inferior | good | inferior |
| (K) | 0.105 | 0.005 | 98.94 | inferior | good | inferior |
| (L) | 0.099 | 0.003 | 99.05 | inferior | good | inferior |
| (M) | 0.082 | 0.001 | 99.22 | inferior | good | inferior |
| (N) | 0.125 | 0.006 | 98.88 | inferior | good | inferior |
| (O) | 0.150 | 0.007 | 98.80 | inferior | good | inferior |
| (P) | 0.112 | 0.005 | 98.91 | inferior | good | inferior |
| (Q) | 0.069 | ≤0.001 | 99.32 | inferior | good | inferior |
| (R) | 0.078 | 0.002 | 99.03 | inferior | good | inferior |

TABLE 3

| NCA | Residual chlorine concentration after purification (mass %) | Purity after purification (mol %) | Purity after a half year from purification (mol %) | Purity after 1 year from purification (mol %) | Purity after 2 years from purification (mol %) |
|---|---|---|---|---|---|
| (A) | 0.005 | 98.93 | 98.94 | 98.92 | 98.90 |
| (B) | ≤0.001 | 99.40 | 99.40 | 99.41 | 99.40 |
| (C) | 0.001 | 99.20 | 99.22 | 99.22 | 99.21 |
| (D) | 0.004 | 99.00 | 98.95 | 99.00 | 99.05 |
| (E) | 0.005 | 98.90 | 98.89 | 98.88 | 98.89 |
| (F) | 0.002 | 99.10 | 99.12 | 99.12 | 99.12 |
| (G) | ≤0.001 | 99.25 | 99.25 | 99.26 | 99.25 |
| (H) | 0.001 | 99.18 | 99.17 | 99.16 | 99.16 |
| (I) | ≤0.001 | 99.35 | 99.35 | 99.36 | 99.36 |
| (J) | 0.002 | 99.10 | 99.15 | 99.12 | 99.10 |
| (K) | 0.005 | 98.94 | 98.90 | 98.92 | 98.93 |
| (L) | 0.003 | 99.05 | 99.02 | 99.04 | 99.05 |
| (M) | 0.001 | 99.22 | 99.23 | 99.23 | 99.23 |
| (N) | 0.006 | 98.88 | 98.85 | 98.86 | 98.85 |
| (O) | 0.007 | 98.80 | 98.77 | 98.79 | 98.79 |
| (P) | 0.005 | 98.91 | 98.92 | 98.90 | 98.91 |
| (Q) | ≤0.001 | 99.32 | 99.33 | 99.33 | 99.33 |
| (R) | 0.002 | 99.03 | 99.07 | 99.06 | 99.05 |

[Long-Term Storage Stability]

Each purified NCA was evaluated for long-term storage stability. Table 3 shows stability at −20±5° C., and Table 4 shows stability at 0 to 5° C. Regarding the conditions of −20±5° C., the results of purity measured by DSC at after a half year, after 1 year, and after 2 years are shown. Regarding the conditions of 0 to 5° C., the results of purity measured by DSC at after 1 month, 2 months, and a half year are shown. As a comparison, commercially available NCA shown by the general formula (A) (manufactured by Isochem), the purity of which is more than 98 mol % based on the DSC measurement, was evaluated and shown as Comparison 1. This NCA has a residual chlorine concentration of 0.030 mass % and belongs to a lot with extremely low TABLE 3-continued

| NCA | Residual chlorine concentration after purification (mass %) | Purity after purification (mol %) | Purity after a half year from purification (mol %) | Purity after 1 year from purification (mol %) | Purity after 2 years from purification (mol %) |
|---|---|---|---|---|---|
| Comparison 1 | 0.030 | 98.14 | 98.06 | 98.02 | <98 |

TABLE 4

| NCA | Residual chlorine concentration after purification (mass %) | Purity after purification (mol %) | Purity after 1 month from purification (mol %) | Purity after 2 months from purification (mol %) | Purity after a half year from purification (mol %) |
|---|---|---|---|---|---|
| (A) | 0.005 | 98.93 | 98.93 | 98.92 | 98.90 |
| (B) | ≤0.001 | 99.40 | 99.39 | 99.41 | 99.41 |
| (C) | 0.001 | 99.20 | 99.22 | 99.21 | 99.19 |
| (D) | 0.004 | 99.00 | 98.98 | 99.00 | 98.95 |
| (E) | 0.005 | 98.90 | 98.90 | 98.88 | 98.86 |
| (F) | 0.002 | 99.10 | 99.12 | 99.10 | 99.10 |
| (G) | ≤0.001 | 99.25 | 99.24 | 99.25 | 99.26 |
| (H) | 0.001 | 99.18 | 99.19 | 99.19 | 99.18 |
| (I) | ≤0.001 | 99.35 | 99.35 | 99.36 | 99.36 |
| (J) | 0.002 | 99.10 | 99.12 | 99.10 | 99.08 |
| (K) | 0.005 | 98.94 | 98.93 | 98.92 | 98.90 |
| (L) | 0.003 | 99.05 | 99.07 | 99.05 | 99.07 |
| (M) | 0.001 | 99.22 | 99.23 | 99.22 | 99.24 |
| (N) | 0.006 | 98.88 | 98.88 | 98.86 | 98.86 |
| (O) | 0.007 | 98.80 | 98.77 | 98.75 | 98.73 |
| (P) | 0.005 | 98.91 | 98.93 | 98.94 | 98.94 |
| (Q) | ≤0.001 | 99.32 | 99.31 | 99.31 | 99.32 |
| (R) | 0.002 | 99.03 | 99.05 | 99.04 | 99.03 |
| Comparison 1 | 0.030 | 98.14 | <98 | <98 | <98 |

Comparative Example 1

Purification was tried in the same way as in Example 1 except that a filter aid was not used, but the filtration was failed because the filter paper caused clogging during vacuum filtration.

Comparative Example 2

Purification was tried in the same way as in Example 1 except for changing the solvent used for dissolving an NCA from ethyl acetate to toluene, but the NCA was not dissolved in toluene.

Comparative Example 3

In the same way as in Example 1 except for changing the solvent used for dissolving an NCA from ethyl acetate to chloroform, 3.80 g of NCA in which impurities were removed was obtained. It was impossible to utilize DSC measurement to determine the purity of the NCA in which impurities were removed because the purity was too low (melting point: 102.4° C.). The residual chlorine concentration was 0.578 mass %.

Comparative Example 4

Purification was tried in the same way as in Example 1 except for using 2.5 ml of hydrogen chloride (1 mol/L solution in ethyl acetate) as an additive without using a filter aid, but the filtration was failed because the filter paper caused clogging during vacuum filtration.

Comparative Example 5

In the same way as in Example 1 except for changing magnesium sulfate, which is an acidic filter aid having ability to trap a basic impurity, to a basic filter aid of Celite 503, 3.00 g of NCA in which impurities were removed was obtained. It was impossible to utilize DSC measurement to determine the purity of the NCA in which impurities were removed because the purity was too low (melting point: 102.1° C.). The residual chlorine concentration was 0.060 mass %.

Comparative Example 6

In the same way as in Example 4 except for changing DPR silica, which is an acidic filter aid having ability to trap a basic impurity, to Silica gel (manufactured by KANTO CHEMICAL CO., INC., for column chromatography), 2.90 g of NCA in which impurities were removed was obtained. It was impossible to utilize DSC measurement to determine the purity of the NCA in which impurities were removed because the purity was too low (melting point: 102.0° C.). The residual chlorine concentration was 0.068 mass %.

Using the NCA obtained in Example 1, in which the impurities were removed, polymerization reaction was conducted with the polyethylene glycol derivative shown in the following structural formula (S).

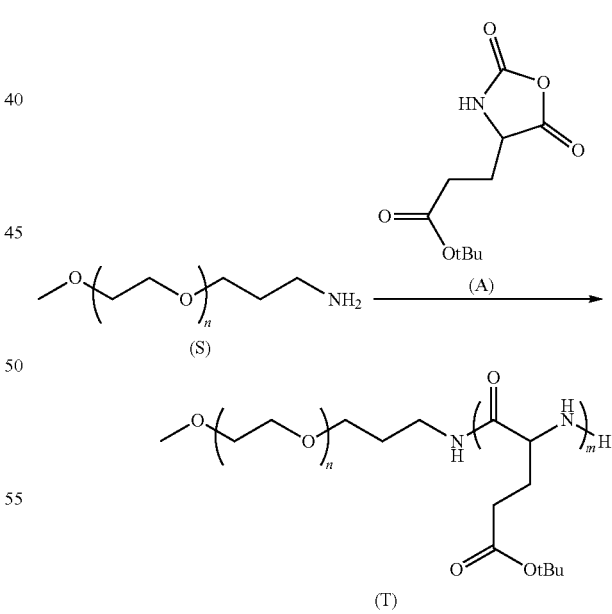

In the following Examples and Comparative Examples, the values of weight average molecular weight (Mw) and number average molecular weight (Mn) were measured by gel permeation chromatography (GPC) in terms of polyethylene glycol. Incidentally, GPC was measured under the following conditions.

Column: TSK gel Super AW3000x2, Super AW-4000
Developing solution: DMF (0.01 mol/L lithium bromide solution)
Temperature of column oven: 40° C.
Concentration of sample: 0.20 wt %
Injection amount of sample: 50 μl
Flow rate: 0.6 ml/min Example 24

A reaction solution was prepared by dissolving 1.01 g of the polyethylene glycol derivative (S) with Mw of about 10,000 to 20 ml of DMF, followed by adding 0.97 g of the NCA obtained in Example 1, in which the impurities were removed. This was subjected to react at 40° C. for 1 day, and then added dropwise to a mixed solvent of 100 ml of ethyl acetate and 200 ml of n-hexane. The produced white powder was filtered and then returned to the original beaker, followed by washing with a mixed solvent of 50 ml of ethyl acetate and 100 ml of n-hexane, together with the same washing repeated for one time. The obtained white powder was vacuum dried to afford 1.00 g of a block copolymer shown by the structural formula (T). The GPC analysis revealed that Mw=13,974 and Mw/Mn=1.12 and did not show a peak of an NCA homopolymer (a polymer which was polymerized due to chloride ion or other basic impurities) at the lower molecular weight region, which is observed in case of using an NCA contaminated with impurities.

Comparative Example 7

In the same way as in Example 24 except for changing the NCA to the unpurified NCA used in Example 1, that is, the NCA contaminated with impurities, as an NCA to be used, 1.04 g of a block copolymer shown by the structural formula (T) was obtained. The GPC analysis revealed that Mw=11,833 and Mw/Mn=1.08. The peak of an NCA homopolymer was observed at the lower molecular weight region, which revealed that Mw=2,117 and Mw/Mn=1.41.

Comparative Example 8

In the same way as in Example 24 except for changing the NCA to an NCA in which the impurities were removed with Celite 503 used in Comparative Example 5, 1.02 g of a block copolymer shown by the structural formula (T) was obtained. The GPC analysis revealed that Mw=12,331 and Mw/Mn=1.09. The peak of an NCA homopolymer was observed at the lower molecular weight region, which revealed that Mw=1,957 and Mw/Mn=1.39.

Comparative Example 9

In the same way as in Example 24 except for changing the NCA to an NCA in which the impurities were removed with Silica gel 60 used in Comparative Example 6, 0.95 g of a block copolymer shown by the structural formula (T) was obtained. The GPC analysis revealed that Mw=12,400 and Mw/Mn=1.09. The peak of an NCA homopolymer was observed at the lower molecular weight region, which revealed that Mw=1,970 and Mw/Mn=1.39.

As shown in Examples 1 to 23, the inventive method for purifying an amino acid-N-carboxyanhydride allowed us to purify a low-purity NCA conveniently to obtain a high-purity NCA. Though the purification operation was conducted in the air, the obtained NCA in which impurities were removed did not cause lowering of the purity. As shown in Example 24, the polymerization reaction using the purified NCA in which impurities were removed by the inventive purification method, having extremely low residual chlorine concentration and content of basic impurities, successfully afforded a high-purity polymer without forming a lower molecular weight NCA homopolymer.

As shown in the results of long term storage stability, it was found that the NCA purified by the inventive purification method, in which the residual chlorine concentration was extremely low and basic impurities were removed, did not cause lowering of the purity even after being left for 2 years at a low temperature of −20° C. and was stable for a half year at a relatively higher temperature of 0 to 5° C. On the other hand, in commercially available NCA having a residual chlorine concentration of 0.03 mass %, the purity was lowered in 2 years at a low temperature of −20° C. and lowered in 1 month at a relatively higher temperature of 0 to 5° C. These results show that the inventive purification method affords an extremely stable NCA with lower residual chlorine concentration in which basic impurities are removed.

On the other hand, in Comparative Example 1 without using a filter aid, the efficiency in filtration was low, and the purification process could not be completed. In Comparative Example 2 using a solvent unable to dissolve an NCA in the step a), the NCA was not dissolved, and the purification process could not be completed. In Comparative Example 3 using chloroform of a chlorinated solvent in the step a), the purified NCA in which the impurities were removed had a high residual chlorine concentration and low purity. In Comparative Example 4 using hydrogen chloride as an additive, the efficiency in filtration was low, and the purification process could not be completed. In Comparative Examples 5 and 6 using a basic filter aid and a filter aid having no ability to trap a basic impurity although being acidic (weakly acidic), purification could not be effected. In Comparative Examples 7 to 9 using a low-purity NCA, the polymerization reaction formed a low molecular NCA homopolymer, which was a by-product.

The above has revealed that the inventive method for purifying an amino acid-N-carboxyanhydride makes it possible to purify a low-purity NCA conveniently to afford a high-purity NCA with higher long term storage stability.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

INDUSTRIAL APPLICABILITY

The NCA purified by the inventive method has extremely low residual chlorine concentration and does not contain basic impurities such as amine. Accordingly, the living ring-opening polymerization thereof does not involve initiation reaction due to an initiator other than the original initiator, and it is possible to synthesize a polypeptide derivative with a uniform molecular weight thereby. The polypeptide derivative with a uniform molecular weight is applicable to various fields that requires a precise material, is especially important in polymer micelle that have to be precisely designed in size, and is applicable to a field of drug delivery system.

The invention claimed is:

1. A method for purifying an amino acid-N-carboxyanhydride shown by the following general formula (1):

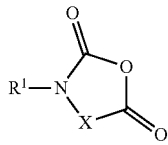

wherein R¹ represents a hydrogen atom, an alkyl group optionally having a substituent, a cycloalkyl group optionally having a substituent, an aryl group optionally having a substituent, a hetero ring optionally having a substituent, or a commonly used protective group for an amino acid selected from a benzyloxycarbonyl group, a t-butoxycarbonyl group, a benzoyl group, and an acetyl group, provided that R¹ does not contain a reactive group of unprotected hydroxy group nor a reactive group of unprotected amino group; X is shown by the following general formula (a) and represents a divalent hydrocarbon group optionally having a substituent, provided that X does not contain a reactive group of unprotected hydroxy group nor a reactive group of unprotected amino group; and R¹ and X are optionally bonded with each other to form a cyclic amino acid structure,

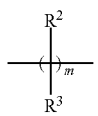

wherein R² and R³ each independently represent a hydrogen atom, an alkyl group optionally having a substituent, a cycloalkyl group optionally having a substituent, an aryl group optionally having a substituent, or a hetero ring optionally having a substituent; and "m" is an integer of 1 to 3, the method comprising the steps of:
a) dissolving the amino acid-N-carboxyanhydride contaminated with impurities into a solvent which is a good solvent for the amino acid-N-carboxyanhydride and is not a chlorinated solvent followed by stirring to precipitate an undissolved impurity to afford a suspension,
b) adding an acidic filter aid having ability to trap a basic impurity to the suspension obtained in the step a) followed by filtration and/or forming a fixed bed of the acidic filter aid having ability to trap a basic impurity followed by filtering the suspension to bring the suspension to be in contact with the acidic filter aid having ability to trap a basic impurity, and
c) adding the filtrate obtained by the step b) dropwise to a poor solvent for the amino acid-N-carboxyanhydride to crystallize out the amino acid-N-carboxyanhydride in which the impurities are removed,
wherein the acidic filter aid having ability to trap a basic impurity used in the step b) is selected from magnesium sulfate, calcium sulfate, barium sulfate, copper sulfate, and silica gel having a surface modified with sulfonic acid or carboxylic acid.

2. The method for purifying an amino acid-N-carboxyanhydride according to claim 1, wherein the amino acid-N-carboxyanhydride is α-amino acid-N-carboxyanhydride, with the "m" being 1.

3. The method for purifying an amino acid-N-carboxyanhydride according to claim 1, wherein the amino acid-N-carboxyanhydride is a compound shown by any of the following structural formulae:

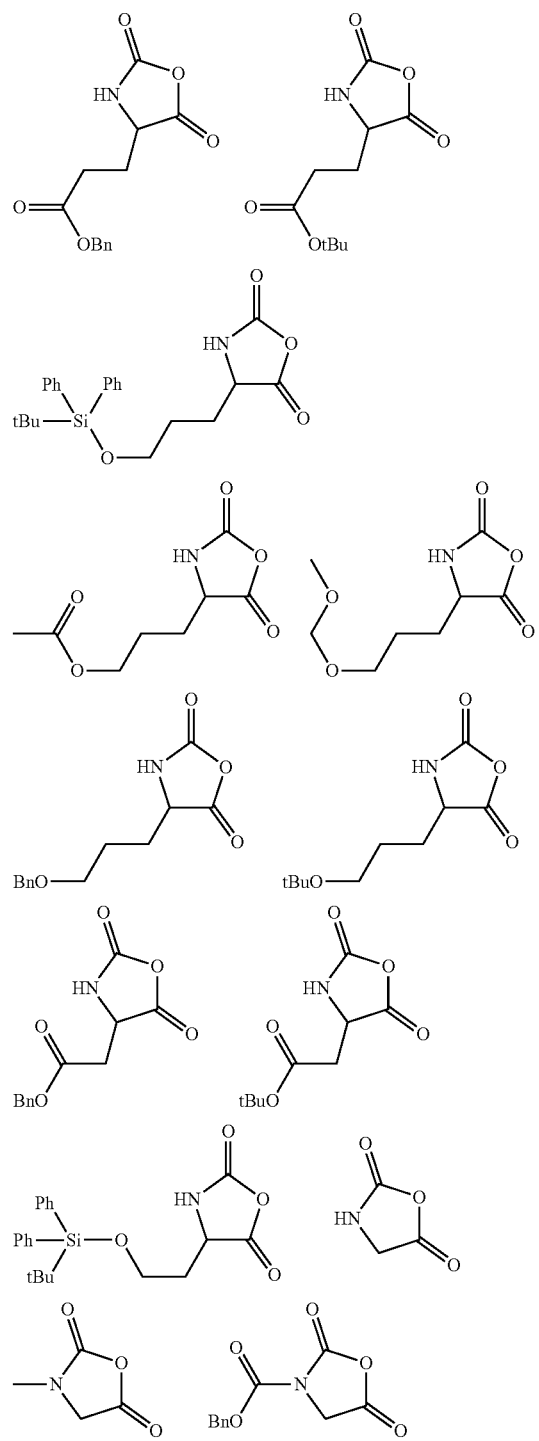

-continued

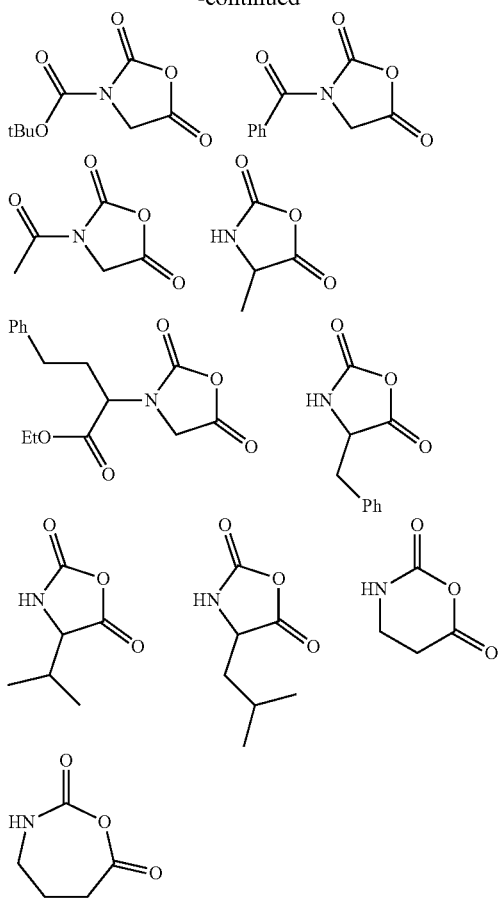

wherein Bn represents a benzyl group, tBu represents a tert-butyl group, Et represents an ethyl group, and Ph represents a phenyl group.

4. The method for purifying an amino acid-N-carboxyanhydride according to claim 1, wherein a mass of the good solvent for the amino acid-N-carboxyanhydride used in the step a) is 1 time or more relative to a mass of the used amino acid-N-carboxyanhydride.

5. The method for purifying an amino acid-N-carboxyanhydride according to claim 2, wherein a mass of the good solvent for the amino acid-N-carboxyanhydride used in the step a) is 1 time or more relative to a mass of the used amino acid-N-carboxyanhydride.

6. The method for purifying an amino acid-N-carboxyanhydride according to claim 3, wherein a mass of the good solvent for the amino acid-N-carboxyanhydride used in the step a) is 1 time or more relative to a mass of the used amino acid-N-carboxyanhydride.

7. The method for purifying an amino acid-N-carboxyanhydride according to claim 1, wherein the good solvent for the amino acid-N-carboxyanhydride used in the step a) is a polar solvent selected from tetrahydrofuran, 1,4-dioxane, ethyl acetate, n-butyl acetate, γ-butyrolactone, acetone, methyl ethyl ketone, methyl isobutyl ketone, dimethyl sulfoxide, N,N-dimethylformamide, and acetonitrile.

8. The method for purifying an amino acid-N-carboxyanhydride according to claim 1, wherein a mass of the poor solvent for the amino acid-N-carboxyanhydride used in the step c) is 2 times or more relative to a mass of the used amino acid-N-carboxyanhydride.

9. The method for purifying an amino acid-N-carboxyanhydride according to claim 1, wherein the poor solvent for the amino acid-N-carboxyanhydride used in the step c) is a solvent selected from n-hexane, n-heptane, n-octane, n-nonane, n-decane, cyclopentane, cyclohexane, cycloheptane, cyclooctane, diethyl ether, diisopropyl ether, and t-butyl methyl ether.

10. The method for purifying an amino acid-N-carboxyanhydride according to claim 1, wherein the amino acid-N-carboxyanhydride in which the impurities are removed has a residual chlorine concentration of 0.05 mass % or less.

11. The method for purifying an amino acid-N-carboxyanhydride according to claim 10, wherein the amino acid-N-carboxyanhydride in which the impurities are removed has a residual chlorine concentration of 0.01 mass % or less.

12. The method for purifying an amino acid-N-carboxyanhydride according to claim 1, wherein the amino acid-N-carboxyanhydride in which the impurities are removed has a purity of 98 mol % or more measured by differential scanning calorimetry.

13. The method for purifying an amino acid-N-carboxyanhydride according to claim 1, wherein the steps a), b), and c) are performed in the air.

* * * * *